(12) United States Patent
Choi et al.

(10) Patent No.: US 8,790,687 B2
(45) Date of Patent: Jul. 29, 2014

(54) TRITERPENE COMPOUNDS WHICH ARE EFFECTIVE ON IMPROVEMENT OF BRAIN FUNCTION

(75) Inventors: Wonrack Choi, Seoul (KR); Chang-Kyun Han, Seoul (KR); Tae Kon Kim, Suwon-si (KR); Guang-Jin Im, Ansan-si (KR); Chil Mann Jung, Suwon-si (KR); Se Jun Yun, Seoul (KR); Bongcheol Kim, Gwacheon-si (KR); Soomin Lee, Seoul (KR); Wie-Jong Kwak, Seoul (KR)

(73) Assignee: SK Chemicals Co., Ltd., Kyungki-Do (KR)

( * ) Notice: Subject to any disclaimer, the term of this patent is extended or adjusted under 35 U.S.C. 154(b) by 239 days.

(21) Appl. No.: 12/643,687

(22) Filed: Dec. 21, 2009

(65) Prior Publication Data

US 2010/0099763 A1 Apr. 22, 2010

Related U.S. Application Data

(63) Continuation of application No. 10/575,384, filed as application No. PCT/KR2004/002590 on Oct. 11, 2004, now abandoned.

(30) Foreign Application Priority Data

Oct. 10, 2003 (KR) .......................... 10-2003-0070612

(51) Int. Cl.
*A61K 47/00* (2006.01)
*A61K 31/56* (2006.01)
*A23L 1/30* (2006.01)

(52) U.S. Cl.
CPC . *A23L 1/30* (2013.01); *A61K 31/56* (2013.01); *A23V 2002/00* (2013.01)
USPC .......................................... 424/439; 514/182

(58) Field of Classification Search
USPC .......................................... 424/439; 514/182
See application file for complete search history.

(56) References Cited

U.S. PATENT DOCUMENTS

| 4,606,911 | A | 8/1986 | Hayashi et al. |
| 5,948,460 | A | 9/1999 | Kang et al. |
| 6,607,758 | B2 | 8/2003 | Castillo et al. |
| 2002/0042535 | A1 | 4/2002 | Gribble et al. |
| 2002/0110604 | A1* | 8/2002 | Babish et al. ............. 424/725 |

FOREIGN PATENT DOCUMENTS

| KR | 10-1996-0004027 B | 3/1996 |
| KR | 10-2003-0042123 A | 5/2003 |
| KR | 10-0424503 B | 6/2004 |

OTHER PUBLICATIONS

Tomassoni, Daniele et al.: "Morphological and conduction changes in the sciatic nerve of spontaneously hypertensive rats", *Neuroscience Letters* 362 (2004), pp. 131-135.

(Continued)

*Primary Examiner* — San-Ming Hui
(74) *Attorney, Agent, or Firm* — Frommer Lawrence & Haug LLP; Ronald R Santucci

(57) ABSTRACT

The present invention relates to the triterpene compounds improving in brain functions. In particular, the present invention relates to a novel use of the triterpene compounds represented by the Formula 1 for improving decreased memory and a pharmaceutical composition for improving brain functions comprising the triterpene compounds represented by the Formula 1.

11 Claims, 1 Drawing Sheet

(56) References Cited

OTHER PUBLICATIONS

Heo, Ho-Jin et al.: "Ursolic Acid of *Origanum majorana* L. Reduces Aâ-induced Oxidative Injury". *Mol. Cells*, vol. 13, No. 1, pp. 5-11.

Qian, Yi-Hua et al.: "The effects of the total saponin of *Dipsacus asperoides* on the damage of cultured neurons induced by β-amyloid protein 25-35", *Anatomical Science International* (2002), 77, pp. 196-200.

Chung, Yo-Kyung et al.: "Inhibitory Effect of Ursolic Acid Purified from *Origanum majorana* L. on the Acetylcholinesterase", *Mol. Cells*, vol. 11, No. 2, pp. 137-143.

Tapondjou, L.A. et al.: "In Vivo Anti-Nociceptive and Anti-Inflammatory Effect of the Two Triterpenes, Ursolic Acid and 23-Hydroxyursolic Acid, from *Cussonia bancoensis*", *Arch Pharm Res*, vol. 26, No. 2, 2003, pp. 143-146.

Li, Jie et al.: "Effects of ursolic acid and oleanolic acid on human colon carcinoma cell line HCT 15", *World J Gastroenterol*, 2002; 8 (3), pp. 493-495.

Kapil, Aruna et al.: "Effect of Oleanolic Acid on Complement in Adjuvant- and Carrageenan-induced Inflammation in Rats", *J. Pharm. Pharmacol* 1995, 47: pp. 585-587.

Kitani, Kenichi et al.: "Pharmacological modifications of endogenous antioxidant enzymes with special reference to the effects of deprenyl: a possible antioxidant strategy", *Mechanisms of Ageing and Development*, 111 (1999), pp. 211-221.

Kashtwada, Yoshiki et al.: "Anti-AIDS Agents 38. Anti-HIV Activity of 3-*O*-Acyl Ursolic Acid Derivatives", *J.Nat.Prod.*, 2000, 63, pp. 1619-1622.

\* cited by examiner

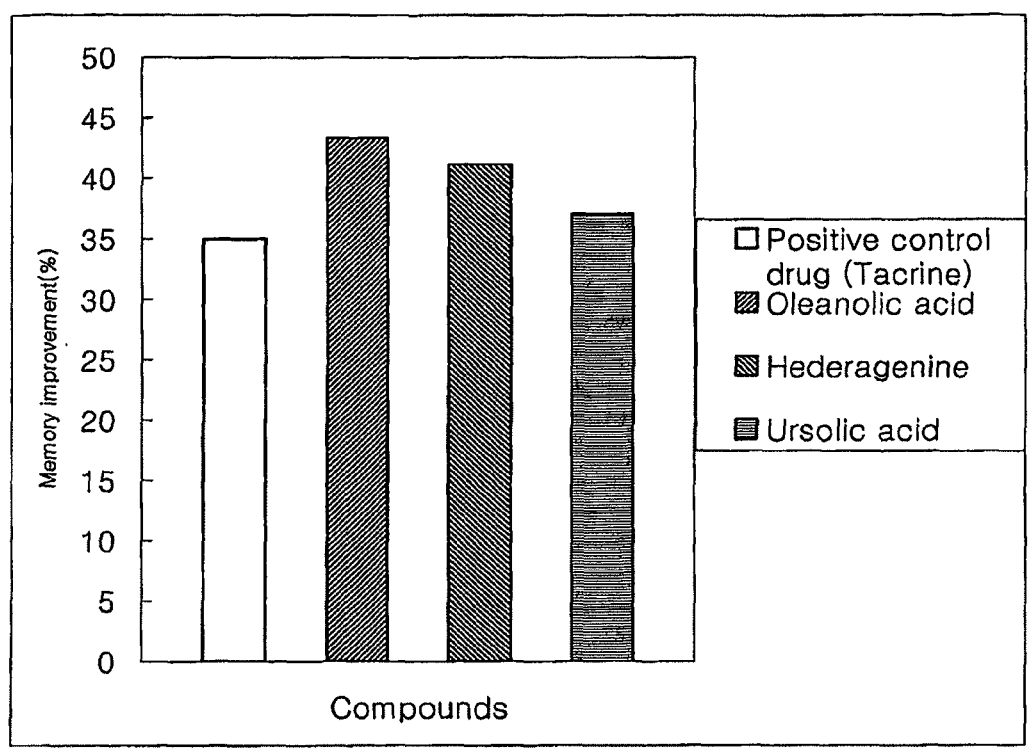

TRITERPENE COMPOUNDS WHICH ARE EFFECTIVE ON IMPROVEMENT OF BRAIN FUNCTION

This application is a continuation of U.S. patent application Ser. No. 10/575,384 filed Feb. 21, 2007 now abandoned entitled "Triterpene Compounds Which are Effective on Improvement of Brain Function", which is a 371 filing of PCT/KR2004/002590 filed Oct. 11, 2004 which claims priority to Korean Application No. 10-2003-0070612 filed Oct. 10, 2003, the disclosures of which are herein incorporated by reference.

BACKGROUND OF THE INVENTION

1. Field of the Invention

The present invention relates to triterpene compounds which can improve brain functions, in particular to a novel use of the triterpene compounds represented by the Formula 1 for improving decreased memory and a pharmaceutical composition for improving brain functions comprising the triterpene compounds represented by the Formula 1.

2. Description of the Related Art

As the percentage of elderly people in population increases over the world, various degenerative senile diseases and disorders have been drawing much of public attention by causing great loss both in social and economic points of view. According to recent results of statistical researches reported by the American Dementia Association and the National Aging Research Institute, four million Americans are suffering from dementia, which is generally developed after the age of sixty and sometimes developed even in fifties. 10.3% of Americans aged 65 years or higher are diagnosed as having dementia and the annual expense for treating dementia in USA amounts to ninety five billion US dollars.

According to the recent reports released by the Korea Institute for Health and Social Affairs, the number of people having dementia is on rapid increase in Korea according to the increase in the number of aged people. For example, the incidence of dementia was 8.3% for a group of people aged 65 or higher in 1995, and it is expected to reach 9% in 2020. In addition, when applying the dementia incidence to the future estimated population reported by the Korea National Statistical Office, the number of elderly people with dementia was two hundred and seventy-seven thousand and forty eight in 2000 (accounting for 8.3% of people aged 65 years or higher), and is presumed to reach five hundred and twenty-seven thousand and sixty eight in 2015 (9%), six hundred and nineteen thousand one hundred and thirty-two in 2020 (9%). Dementia is a disease known very hard to cure and causes to devastate the life of its patient as well as to disrupt a life of his/her family, thereby leading to serious social and economical problems.

Moreover, mild cognitive impairment (MCI) as a pre-stage of dementia is characterized by a less cognitive function such as memory, perception and learning than normal aged people, being not consistent with the clinical standards of dementia. Recent clinical studies have shown that patients with mild cognitive impairment are very susceptible to development of dementia. Patients diagnosed as having mild cognitive impairment are often linked to development of dementia in a ratio of 10-15% as compared to a normal control group which is in a ratio of 1-2%. Therefore, for preventing and treating dementia, it is very important that patients with mild cognitive impairment considered as a susceptible group to dementia be treated at its early stage.

While the pathology of dementia is diverse, its principle cause is known to be Alzheimer's disease the characteristics of which include accumulation of the beta-amyloid protein in brain cells and remarkable decrease in learning and memory capabilities.

As a drug for treating Alzheimer's disease, the FDA-approved drug tacrine, which has been commercially available since 1993, inhibits degradation of acetylcholine generated in brain of Alzheimer's patients at its early and middle stages to delay the loss of cognitive function in about 30% of patients. However, the drug elicits adverse effects associated with liver so that its administration rarely performs. Aricept approved by US FDA in 1996 exhibits its effect by increasing the availability of acetylcholine and its administration may be performed once a day before retirement, showing the adverse effects such as nausea, diarrhea and fatigue that are not severe and likely to disappear soon. However, both tacrine and aricept cannot treat Alzheimer's disease completely and their administration period and effective duration are not obvious.

Therefore, there is an urgent need in the art to develop a novel agent for improving brain functions to prevent and treat mild cognitive impairment and dementia.

The present inventors have made extensive researches to develop a pharmaceutical composition effective in improvement of memory with little adverse effects to improve brain functions such as the prevention and treatment of mild cognitive impairment and dementia and as a result, discovered that existing triterpene compounds are effective in the improvement of memory failure.

Accordingly, it is an object of this invention to provide a pharmaceutical composition for improving brain functions, which comprises as an active ingredient a triterpene compound represented by the Formula 1.

It is another object of this invention to provide an agent for improving brain functions, which comprises as an active ingredient a triterpene compound represented by the Formula 1.

It is still another object of this invention to provide an agent for preventing and treating mild cognitive impairment and dementia, which comprises as an active ingredient a triterpene compound represented by the Formula 1.

It is further object of this invention to provide an agent for preventing and treating dementia, which comprises as an active ingredient a triterpene compound represented by the Formula 1.

It is still further object of this invention to provide a health food for improving brain functions, which comprises as an active ingredient a triterpene compound represented by the Formula 1.

DETAILED DESCRIPTION OF THIS INVENTION

In one aspect of this invention, there is provided a pharmaceutical composition for improving brain functions, which comprises as an active ingredient a triterpene compound represented by the Formula 1:

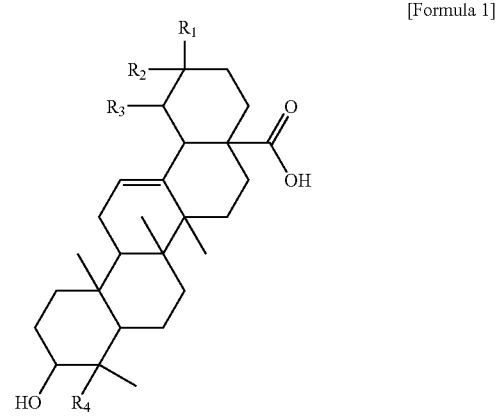

[Formula 1]

wherein $R_1$, $R_2$ and $R_4$ are independently $CH_3$ and $R_3$ is H; $R_1$ and $R_2$ are independently $CH_3$, $R_3$ is H and $R_4$ is $CH_2OH$; or $R_1$, $R_3$ and $R_4$ are independently $CH_3$ and $R_2$ is H.

The present invention will be described in more detail hereunder.

The present inventor relates to a novel use of the triterpene compounds represented by the Formula 1 for improving decreased memory and a pharmaceutical composition for improving brain functions comprising the triterpene compounds represented by the Formula 1. The specific example of triterpene compounds of the Formula 1 includes oleanolic acid, hederagenine and ursolic acid represented by the following Formulae (1a), (1b) and (1c), respectively:

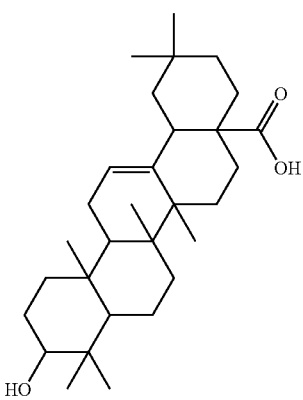

(1a)

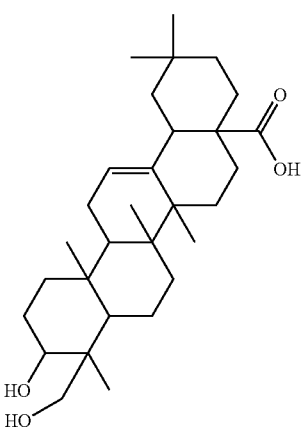

(1b)

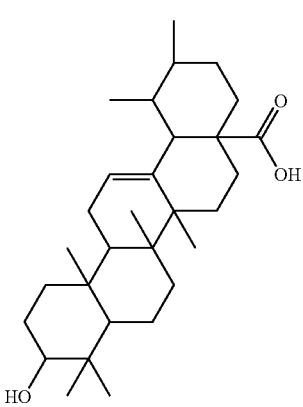

(1c)

Oleanolic acid (1a) is a compound belonging to oleanane-based triterpene, showing anticancer and anti-inflammation effects [Li J, Guo W J, Yang Q Y. Effects of ursolic acid and oleanolic acid on human colon carcinoma cell line HCT15. World J Gastroenterol. 2002 June;8(3):493-5], neuron protection [Qian Y H, Liu Y, Hu H T, Ren H M, Chen X L, Xu J H. The effects of the total saponin of Dipsacus asperoides on the damage of cultured neurons induced by beta-amyloid protein 25-35], antiviral activity [Kapil A, Sharma S. Effect of oleanolic acid on complement in adjuvant- and carrageenan-induced inflammation in rats. J Pharm Pharmacol. 1995 July; 47(7):585-7] and antiangiogenesis activity [Korean Patent No. 101480].

Hederagenine (1b) is a compound belonging to oleanane-based triterpene and its efficacy has not been known yet.

Ursolic acid (1c) is a compound belonging to ursane-based triterpene and known to exhibit anti-inflammatory effect [Tapondjou L A, Lontsi D, Sondengam B L, Choi J, Lee K T, Jung H J, Park H J. In vivo anti-nociceptive and anti-inflammatory effect of the two triterpenes, ursolic acid and 23-hydroxyursolic acid, from Cussonia bancoensis. Arch Pharm Res. 2003 February;26(2):143-6], antiviral activity [Kashiwada Y, Nagao T, Hashimoto A, Ikeshiro Y, Okabe H, Cosentino L M, Lee K H. Anti-AIDS agents 38. Anti-HIV activity of 3-O-acyl ursolic acid derivatives. J Nat Prod. 2000 December;63(12):1619-22], brain neuron protection [Chung Y K, Heo H J, Kim E K, Kim H K, Huh T L, Lim Y, Kim S K, Shin D H. Inhibitory effect of ursolic acid purified from Origanum majorana L on the acetylcholinesterase. Mol Cells. 2001 April 30;11(2):137-43.] and prevention of cancer metastasis [Korean Pat. Appln. No. 1996-0054598].

However, the compounds of this invention described above have not been reported to exert the improvement efficacy in brain functions such as the prevention and treatment of mild cognitive impairment and dementia.

According to the animal test, where the control not subject to the administration of scopolamine and drugs was considered 100% and the group subject to the administration of scopolamine (1 mg/kg), known to result in the failure of memory through the inhibition of transmission of neurotransmitters, was considered 0%, the groups subject to the administration of oleanolic acid, hederagenine, ursolic acid or tacrine after 1 hr of the administration of scopolamine were measured to exhibit significant memory improvement of 43.3%, 41.1% and 37.0%, respectively.

Therefore, it can be recognized that the triterpene compounds represented by the Formula 1 is useful as an agent for preventing and treating mild cognitive impairment and dementia and an agent for improving brain functions.

Where formulating a pharmaceutical composition, the triterpene compounds represented by the Formula 1 may be administered in an oral or parenteral manner and formulated in a form of general drugs.

For a clinical administration, the triterpene compounds represented by the Formula 1 may be administered in various forms for oral or parenteral administration. For formulation, a conventional filler, an expander, a binder, a wetting agent, a disintegrator, a surfactant, a diluent and a carrier may be used.

An oral solid formulation includes tablet, pill, powder, granule and capsule, which are prepared by formulating lignan, lactone compound and its derivative with at least one carrier such as starch, calcium carbonate, sucrose, lactose and gelatin. In addition, a lubricant such as magnesium stearate and talc as well as conventional carrier is used. An oral solution formulation includes suspension, enteric solution, emulsion and syrup, which are prepared by formulating water as diluent, aqueous paraffin and various carriers such as wetting agent, flavor, aromatic agent and preservative.

A parenteral formulation includes sterilized solution, non-aqueous solution, suspension, emulsion, frozen-dried preparation and suppository. For non-aqueous solution and suspension, propylene glycol, polyethylene glycol, plant oil such as olive oil and injectable ester such as ethyl olerate may be used. As a base for suppository, Weetepsol, Macrogol, Tween 61, cacao butter, laurin butter and glycerinated gelatin may be employed.

The amount of the active ingredient of this invention in the formulation may be selected depending on absorption rate, inactivation rate, excretion rate, and age, sex and condition of patients. The triterpene compounds represented by the Formula 1 may be administered once, twice or three times a day in a dosage of 0.1-10 mg/kg, preferably, 0.5-5 mg/kg.

In another aspect of the present invention, there is provided a health food for improving brain functions, which comprises as an active ingredient a triterpene compound represented by the Formula 1.

The term, health food means a food exhibiting a specific efficacy when ingested, manufactured by incorporating into general foods a triterpene compound represented by the Formula 1 or formulating the compound to capsule, powder and suspension. The health food has no or little adverse effects generally associated with long-term drug application.

BRIEF DESCRIPTION OF THE DRAWINGS

FIG. 1 represents a graph showing the improvements in decreased memory by scopolamine, with oral single administration of each of oleanolic acid (1a), hederagenine (1b) and ursolic acid (1c)

EXAMPLES

The following specific examples are intended to be illustrative of the invention and should not be construed as limiting the scope of the invention as defined by appended claims.

Example 1

Passive Avoidance Test

To verify whether oleanolic acid, hederagenine and ursolic acid may improve in vivo the failure of memory associated with mild cognitive impairment and dementia, the passive avoidance test was carried out.

A shuttle box (50×15×40 cm) was used as an experimental device. The box was divided into two rooms by a guillotine door, where one of which was bright by illumination while the other was dark by black cloth, giving rise to two different illumination effects.

Firstly, mice were placed into a bright room, the bright room was kept lighted and the guillotine door was kept open. The mice entered the dark room in 20 sec in accordance with their negative phototaxis and the guillotine door was kept closed upon the entrance. The latency period in which a mouse enters the dark room from the bright room was measured in a manner described above. On the first day of the test, all mice were subject to a training trial for 20-sec latency period.

Next day, mice subject to the training trial were again placed in the bright room and the bright room was then kept lighted to render mice to enter the dark room. At this time, the electric shock of 0.8 mA was imposed for 3 sec by using an electric grid equipped on the bottom of the dark room to impose the electric shock on the sole of mice feet.

After 24 hr of such acquisition trial, mice were again placed in the bright room and the bright room was then kept lighted to induce mice to enter the dark room. At this time, normal mice hesitated to enter the dark room due to the memory about the shock of the previous day. The latency period was measured with the maximum value of 300 sec.

The control not subject to the administration of scopolamine and drugs was considered 100% and the group subject to the administration of scopolamine (1 mg/kg), known to result in the failure of memory through the inhibition of transmission of neurotransmitters, was considered 0%. The groups subject to the administration of oleanolic acid, hederagenine, ursolic acid or tacrine after 1 hr of the administration of scopolamine were tested to measure the memory improvement.

As a result, it was elucidated that the group subject to oral administration of tacrine (30 mg/kg) as a positive control drug exhibited 35% prevention efficacy to memory failure and oleanolic acid, hederagenine and ursolic acid of the present invention also showed 43.3%, 41.1% and 37.0% prevention activity, respectively (see FIG. 1).

On the basis of the results discussed previously, it could be appreciated that oleanolic acid, hederagenine and ursolic acid have a capacity of improving a memory failure associated with mild cognitive impairment and dementia.

Example 2

Toxicity Test

Oleanolic acid, hederagenine and ursolic acid were orally administered seven times into ICR mice (body weight 25-30 g, 5 male mice per unit dose, BGI, Korea) in the unit dose of 2.0 g/kg, 680 mg/kg, 230 mg/kg and 75 mg/kg, respectively, for 1 week and on that day, mice treated were observed with naked eyes in an interval of 30 min. Furthermore, for 2 weeks after the administration, the death rate, general conditions and body weight of mice were examined and abnormality of organs was observed via autopsy.

It was elucidated that $LD_{50}$ of oleanolic acid, hederagenine and ursolic acid was no less than 5.0 g/kg ($LD_{10}$=750 mg/kg), all dosages gave rise to no disorders and the results of autopsy were not different from the control group.

Preparatory Example 1

Preparation of Powder and Capsule 10 mg of the triterpene compound represented by the Formula 1 were mixed with 14.8 mg of lactose, 3 mg of crystalline cellulose and 0.2 mg of magnesium stearate. The mixture was introduced into No. 5 gelatin capsule by using a suitable apparatus.

The ingredients of powder and capsule were as follows:

| | |
|---|---|
| Active ingredient | 10 mg |
| Lactose | 14.8 mg |
| Crystalline cellulose | 3 mg |
| Magnesium stearate | 0.2 mg |

Preparatory Example 2

Preparation of Injection Solution 10 mg of the triterpene compound represented by the Formula 1, 180 mg of mannitol, 26 mg of $Na_2HPO_4 \cdot 12H_2O$ and 2974 mg of distilled water were mixed to prepare an injection solution. The solution was poured into a bottle and sterilized for 30 min at 20□.

| | |
|---|---|
| Active ingredient | 10 mg |
| Mannitol | 180 mg |
| Na$_2$HPO$_4$·12H$_2$O | 26 mg |
| Distilled water | 2974 mg |

Preparatory Example 3

Preparation of Health Food

For a daily dosage, 0.2 g of the triterpene compound represented by the Formula 1, powderized Vitamin E, ferrous lactate, zinc oxide, nicotinic amide, and Vitamins A, B1 and B2 were mixed to prepare a health food.

The ingredients of the health food are as follows (for a daily dosage in human):

| | |
|---|---|
| Active ingredient | 300 mg |
| Ginseng extract | 100 mg |
| Green tee extract | 100 mg |
| Vitamin C | 100 mg |
| Powdered Vitamin E | 120 mg |
| Ferrous lactate | 2 mg |
| Zinc oxide | 2 mg |
| Nicotinic amide | 20 mg |
| Vitamin A | 5 mg |
| Vitamin B1 | 2 mg |
| Vitamin B2 | 2 mg |
| Corn starch | 200 mg |
| Magnesium stearate | 20 mg |

As described previously, the triterpene compounds of this invention represented by the Formula 1 exhibit the efficacy of the memory improvement, so that they are very useful as an agent or food additive for improving brain functions to prevent and treat mild cognitive impairment and dementia.

What is claimed is:

1. A method of improving brain function which comprises administering to a patient in need thereof a therapeutically effective amount of a triterpene compound represented by the Formula 1:

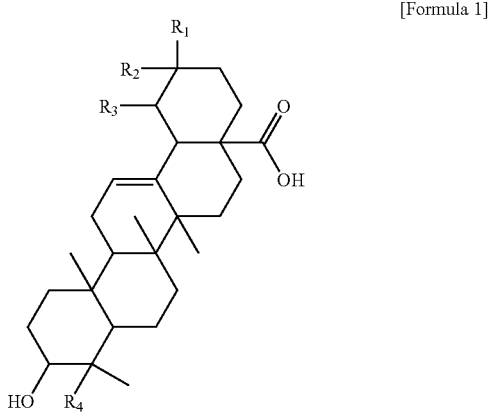

[Formula 1]

wherein R$_1$ and R$_2$ are independently CH$_3$, R$_3$ is H and R$_4$ is CH$_2$OH, and wherein the triterpene compound represented by the Formula 1 is hederagenine.

2. A method of treating mild cognitive impairment or dementia which comprises administering to a patient in need thereof a therapeutically effective amount of a triterpene compound represented by the Formula 1:

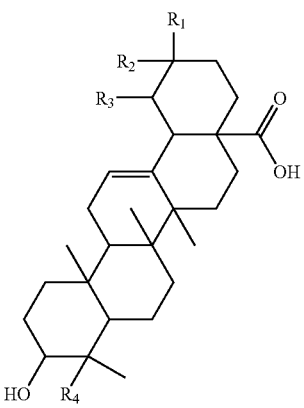

[Formula 1]

wherein R$_1$ and R$_2$ are independently CH$_3$, R$_3$ is H and R$_4$ is CH$_2$OH, and wherein the triterpene compound represented by the Formula 1 is hederagenine.

3. The method of claim 1, wherein the brain function is memory, perception or learning.

4. The method of claim 1, wherein the triterpene compound is administered to a patient in forms of oral or parenteral formulation with at least one a pharmaceutically acceptable carrier or excipient.

5. The method of claim 2, wherein the triterpene compound is administered to a patient in forms of oral or parenteral formulation with at has one a pharmaceutically acceptable carrier or excipient.

6. The method according to claim 1, wherein the triterpene compound is administered to a patient in a capsule formulation with at least one pharmaceutically acceptable carrier or excipient.

7. The method according to claim 1, wherein the triterpene compound is administered to a patient in an injectable formulation with at least one pharmaceutically acceptable carrier or excipient.

8. The method according to claim 1, wherein the triterpene compound is administered to a patient in a health food formulation with at least one pharmaceutically acceptable carrier or excipient.

9. The method according to claim 2, wherein the triterpene compound is administered to a patient in a capsule formulation with at least one pharmaceutically acceptable earner or excipient.

10. The method according to claim 2, wherein the triterpene compound is administered to a patient in an injectable formulation with at least one pharmaceutically acceptable carrier or excipient.

11. The method according to claim 2, wherein the triterpene compound is administered to a patient in a health food formulation with at least one pharmaceutically acceptable carrier or excipient.

* * * * *